United States Patent
Giraud et al.

(10) Patent No.: US 11,590,298 B2
(45) Date of Patent: Feb. 28, 2023

(54) INHALER AND METHODS OF USING AND MAKING SAME

(71) Applicants: CSP Technologies, Inc., Auburn, AL (US); SIMPLIFIED SOLUTIONS SWEDEN AB, Lindome (SE)

(72) Inventors: Jean-Pierre Giraud, Auburn, AL (US); Bruce Rabinne, Boissy-le-Chatel (FR); Yutaka Kataoka, Lindome (SE)

(73) Assignee: CSP Technologies, Inc., Auburn, AL (US)

( * ) Notice: Subject to any disclaimer, the term of this patent is extended or adjusted under 35 U.S.C. 154(b) by 496 days.

(21) Appl. No.: 16/617,636

(22) PCT Filed: Jun. 4, 2018

(86) PCT No.: PCT/US2018/035776
§ 371 (c)(1),
(2) Date: Nov. 27, 2019

(87) PCT Pub. No.: WO2018/223109
PCT Pub. Date: Dec. 6, 2018

(65) Prior Publication Data
US 2020/0139059 A1 May 7, 2020

Related U.S. Application Data

(63) Continuation of application No. PCT/US2018/022732, filed on Mar. 15, 2018.
(Continued)

(51) Int. Cl.
*A61M 15/00* (2006.01)

(52) U.S. Cl.
CPC .... *A61M 15/0048* (2014.02); *A61M 15/0021* (2014.02); *A61M 15/0043* (2014.02);
(Continued)

(58) Field of Classification Search
CPC ........... A61M 15/0043–0051; A61M 15/0021; A61M 15/0075; A61M 2202/062;
(Continued)

(56) References Cited

U.S. PATENT DOCUMENTS 5,911,937 A 6/1999 Hekal
6,080,350 A 6/2000 Hekal
(Continued)

FOREIGN PATENT DOCUMENTS

EP 2712643 A1 4/2014
WO WO-0053248 A1 * 9/2000 ........ A61M 15/0005

OTHER PUBLICATIONS

International Search Report and Written Opinion for International Application No. PCT/US2018/035776, dated Aug. 3, 2018.

*Primary Examiner* — Elliot S Ruddie
(74) *Attorney, Agent, or Firm* — Mark T. Vogelbacker; Eckert Seamans Cherin & Mellot, LLC

(57) ABSTRACT

An inhaler for facilitating inhalation of dry powder includes a body defining an interior space and a mouth piece. At least one annular member is positioned within the interior space and is rotatable with respect to the mouth piece. The at least one annular member includes a plurality of compartments. Each compartment defines a cavity configured to hold dry powder. Each compartment includes at least one flap and an opening configured to release the dry powder when the at least one flap is reconfigured from a closed position to an open position. The at least one flap covers the opening and inhibits the dry powder from being released from the cavity in the closed position.

14 Claims, 13 Drawing Sheets

Related U.S. Application Data

(60) Provisional application No. 62/514,072, filed on Jun. 2, 2017.

(52) U.S. Cl.
CPC ... *A61M 15/0075* (2014.02); *A61M 2202/062* (2013.01); *A61M 2202/064* (2013.01)

(58) Field of Classification Search
CPC ........ A61M 2202/064; A61M 15/0026; A61M 15/0065; A61M 15/0013–0016; A61M 15/002; A61M 15/0091
USPC .................................................... 128/203.15
See application file for complete search history.

(56) References Cited

U.S. PATENT DOCUMENTS

| | | |
|---|---|---|
| 6,124,006 A | 9/2000 | Hekal |
| 6,130,263 A | 10/2000 | Hekal |
| 6,194,079 B1 | 2/2001 | Hekal |
| 6,214,255 B1 | 4/2001 | Hekal |
| 6,486,231 B1 | 11/2002 | Hekal |
| 7,005,459 B2 | 2/2006 | Hekal |
| 9,585,834 B2 | 3/2017 | Morton |
| 2009/0084379 A1 | 4/2009 | Goeckner et al. |
| 2011/0259326 A1* | 10/2011 | Briant ............... A61M 15/0048 128/203.12 |
| 2014/0007875 A1* | 1/2014 | berg .................. A61M 15/0016 128/203.15 |
| 2014/0083423 A1 | 3/2014 | Jung et al. |
| 2016/0039955 A1 | 2/2016 | Klein et al. |

* cited by examiner

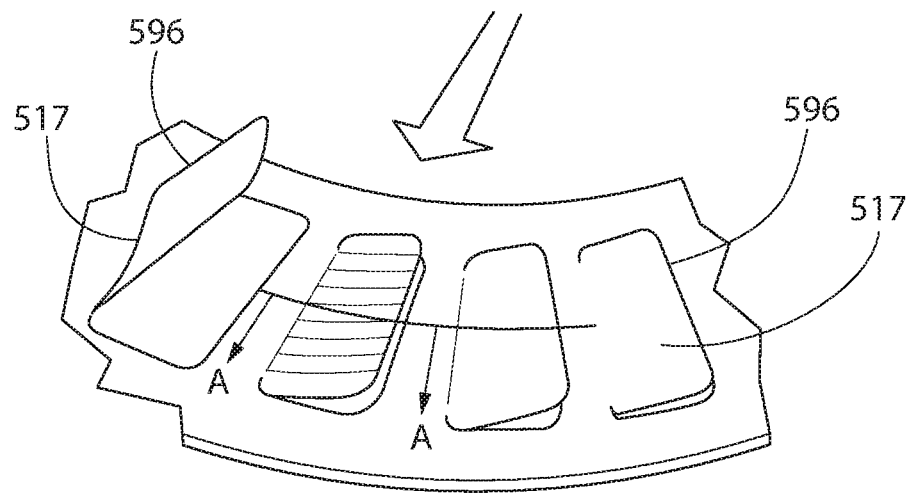
FIG. 19A
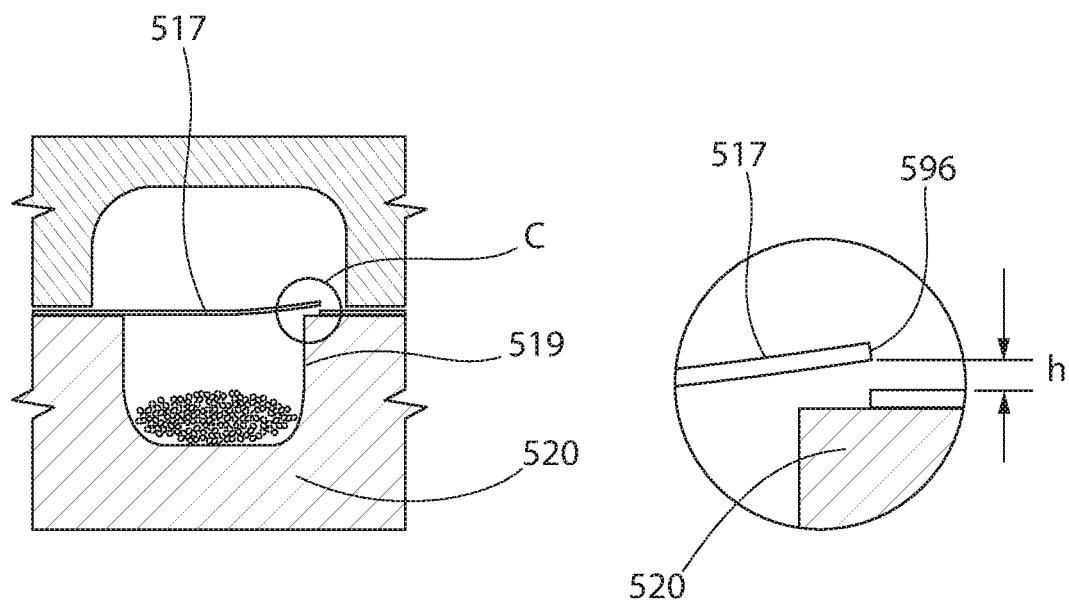
FIG. 19B
FIG. 19C

INHALER AND METHODS OF USING AND MAKING SAME

CROSS-REFERENCE TO RELATED APPLICATIONS

This application is a U.S. National Phase of International Application No. PCT/US2018/035776, titled "INHALER AND METHODS OF USING AND MAKING SAME" and filed Jun. 4, 2018, which claims priority to U.S. Provisional Patent Application No. 62/514,072, titled "METHODS AND DEVICES FOR FACILITATING DESIRABLE POWDERED DOSE RING POCKET CAVITY AIR FLOW" and filed Jun. 2, 2017, and also claims priority to International Patent Application No. PCT/US2018/022732, titled "INHALER AND METHODS OF USING AND MAKING SAME" and filed Mar. 15, 2018, all of which are herein incorporated by reference in their entirety.

FIELD

This presently disclosed technology relates generally to inhalers. More particularly, in one embodiment, the presently disclosed technology relates to methods and devices for facilitating inhalation of dry powder medicament.

BACKGROUND AND DESCRIPTION OF RELATED ART

Dry powder inhalers, or "DPIs," of the prior art provide multiple doses of a powdered drug product to a patient, which a patient self-administers through respiration. U.S. Patent Application Publication No. 2014/0007875, which is incorporated herein by reference in its entirety, describes one prior art DPI, which includes discs having capsules containing dry powder and an apparatus that facilitates dispensing a dose of the powder from one capsule at a time upon inhalation by a user. U.S. Patent Application Publication No. 2009/0084379, which is also incorporated herein by reference in its entirety, discloses a DPI with a single air flow path to facilitate administration of the dry powder.

Although prior art DPIs are useful and can be beneficial, at least one issue with prior art DPIs, particularly those that contain many doses, is that the small volume of each individual powder-containing pocket can make it difficult for such DPIs to function due to insufficient air flow. At least certain prior art dose ring geometry, when filled with the powder and then ultrasonically welded with an aluminum foil disc, may provide insufficient Venturi air flow pattern to allow the pre-cut via laser aluminum foil to lift, to allow the powder to dispense. Each pocket in at least certain prior art designs has only a single opening (i.e., covered by the foil) and an otherwise solid interior wall geometry that does not allow any permeation of air. The powder is only lifted due to a pressure differential of the air above the aluminum foil (and the single opening) being greater than the pressure differential inside the headspace of the cavity.

In previous designs, there is often insufficient pressure differential or air flow to allow the aluminum foil flap to lift and the powder to be dispensed. In addition, necessary sealing means to preserve the product may be configured to impede proper functioning at the time of use if air flow is insufficient.

SUMMARY

There is a need in the art to address the above and other issues of prior art DPIs. The presently disclosed technology achieves the above and other objectives.

In one embodiment, at least one issue of prior art designs is solved by providing an additional air flow path via an air flow entry point (e.g., a second opening) into each pocket cavity. By incorporating an air flow entry point into or adjacent to each pocket, when the user inhales into the air duct, the Venturi air flow pattern velocity across the top of the pre-cut aluminum foil flap, combined with the air flow entry point in or adjacent each pocket, provides sufficient air flow volume to allow the aluminum foil flap to lift. This lifting of the aluminum foil flap, in turn, allows the powder to dispense from the pocket cavity and into the air duct, ultimately into the patient's mouth, thereby administering a metered dose of medicament. In another embodiment, changes are made to the flap configuration of the prior art so improve the ability of a user to receive and/or inhale the medicament One aspect of the presently disclosed technology includes an inhaler for facilitating inhalation of dry powder that has a body defining an interior space and a mouth piece. At least one annular member is positioned within the interior space and is rotatable with respect to the mouth piece. The at least one annular member includes a plurality of compartments. Each compartment defines a cavity configured to hold dry powder. Each compartment includes at least one flap and an opening configured to release the dry powder when the at least one flap is reconfigured from a closed position to an open position. The at least one flap covers the opening and inhibits the dry powder from being released from the cavity in the closed position.

In another aspect, the presently disclosed technology includes an inhaler for facilitating inhalation of dry powder that has a body defining an interior space and a mouth piece. At least one member is positioned within the interior space of the body. The at least one member includes at least one compartment defining a cavity configured to hold dry powder. The at least one compartment including at least one flap and an opening configured to release the dry powder when the at least one flap is reconfigured from a closed position to an open position. The at least one flap covers the opening and inhibits the dry powder from being released from the cavity in the closed position.

In yet another aspect, the presently disclosed technology is directed to a method of administering dry power medicament contained in an inhaler. The inhaler includes a body defining an interior space and a mouth piece. The inhaler further includes at least one member within the interior space of the body. The at least one member includes at least one compartment defining a cavity configured to hold the medicament. The at least one compartment includes at least one flap and an opening configured to release the medicament when the at least one flap is reconfigured from a closed position to an open position. The at least one flap covers the opening and inhibits the medicament from being released from the cavity in the closed position. The method includes inhaling or evacuating air from within the interior space of the body through the mouth piece, thereby causing air to reconfigure the at least one flap from the closed position to the open position and force at least some of the medicament out of the cavity and through the mouth piece.

In still another aspect, the presently disclosed technology is directed to inhaling or evacuating air from within the interior space of the body through the mouth piece, thereby causing air to open at least one flap.

BRIEF DESCRIPTION OF SEVERAL VIEWS OF THE DRAWINGS

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings:

FIG. 19A is perspective view of a portion on an inhaler according to an embodiment of the presently disclosed technology, wherein the left-most flap is shown in FIG. 19A is in an open position and the remaining flaps are shown in a closed position;

FIG. 19B is a cross-sectional side elevation view of a portion of the inhaler shown in FIG. 19A taken along line A-A of FIG. 19A; and FIG. 19C is a magnified view of a portion of the inhaler shown in FIG. 19A.

DETAILED DESCRIPTION

While systems, devices and methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Any headings used herein are for organizational purposes only and are not meant to limit the scope of the description or the claims. As used herein, the word "may" is used in a permissive sense (i.e., meaning having the potential to) rather than the mandatory sense (i.e., meaning must). Unless specifically set forth herein, the terms "a," "an" and "the" are not limited to one element but instead should be read as meaning "at least one." The terminology includes the words noted above, derivatives thereof and words of similar import.

According to one aspect of the presently disclosed technology, the aforementioned problems with previous designs are solved by providing an additional air flow path via an air flow entry point into or adjacent to each pocket cavity. By incorporating an air flow entry point into or adjacent each pocket, when the user inhales into the air duct, the Venturi air flow pattern velocity across the top of the pre-cut aluminum foil flap, combined with the air flow entry point in or adjacent each pocket, will provide sufficient air flow volume to allow the aluminum foil flap to lift. This lifting of the (e.g., aluminum foil) flap, in turn, allows the powder with active product ingredient (API) to dispense from the pocket cavity and into the air duct, ultimately into the patient's mouth, thereby administering a metered dose of powdered API. In another aspect of the presently disclosed technology, an additional air flow path as described above is omitted, but modifications are made the flap geometry or configuration, which allows the flap to be more easily opened by the inhalation of the user, thereby more readily or easily releasing the powder from the pocket cavity. In another embodiment, the modifications to the flap geometry or configuration can be combined with the additional air flow path.

Figure 5:
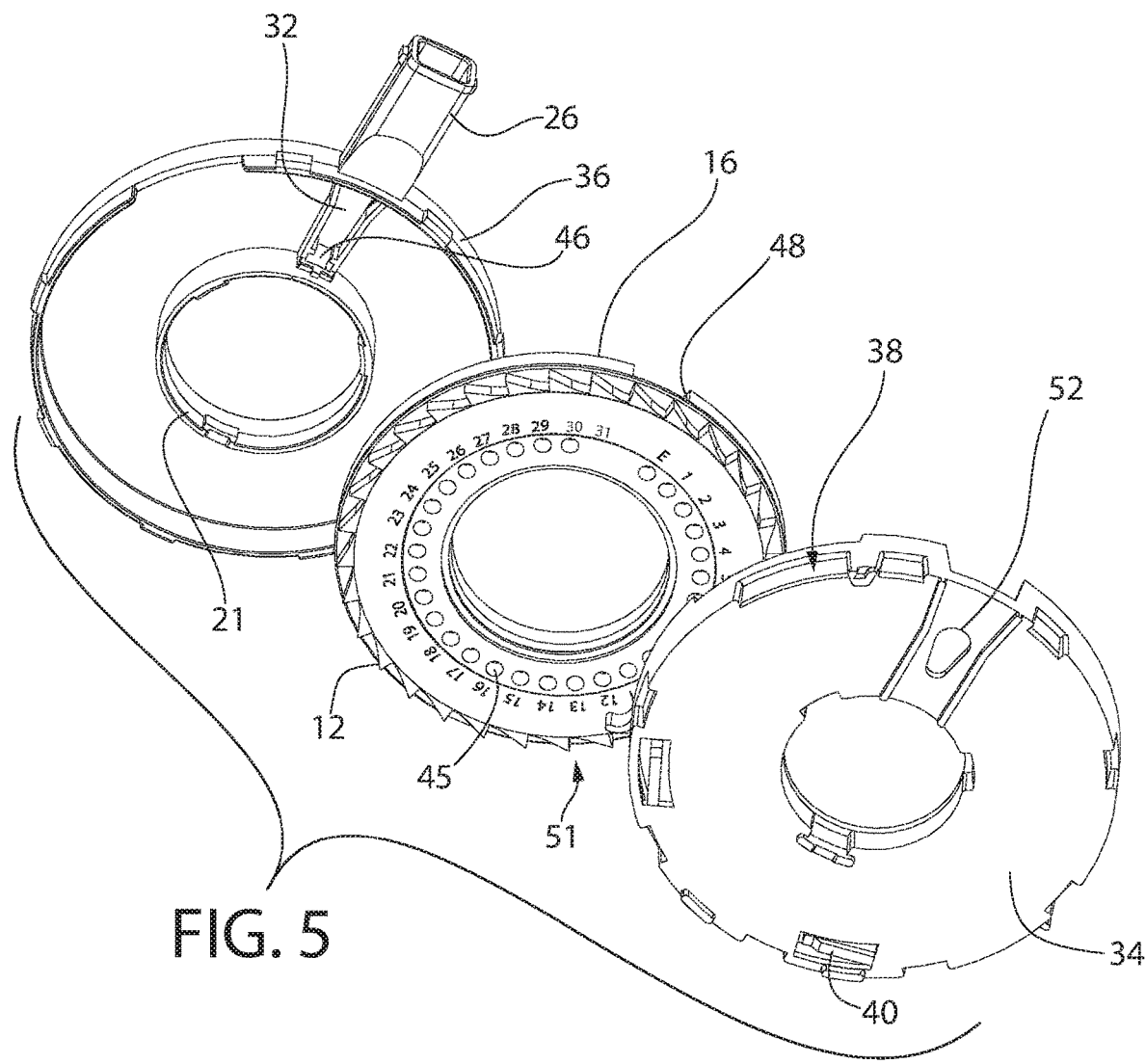
FIG. 5 is another partially exploded perspective view of the interior components shown in FIG. 4, wherein the components are shown from the first side shown in FIG. 1.
Figure 6:
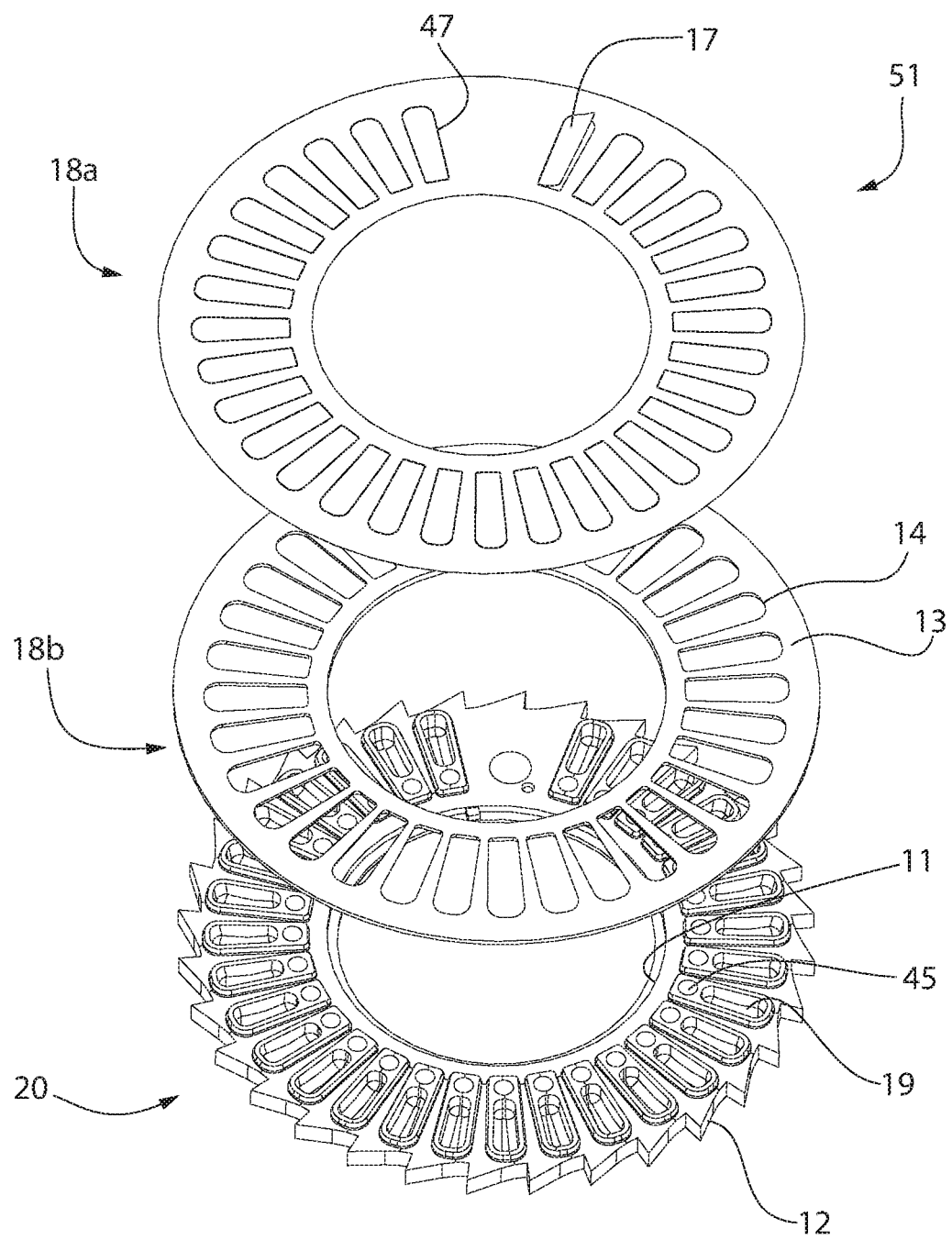
FIG. 6 is a perspective view of an annular member visible in FIGS. 4 and 5.
Figure 7:
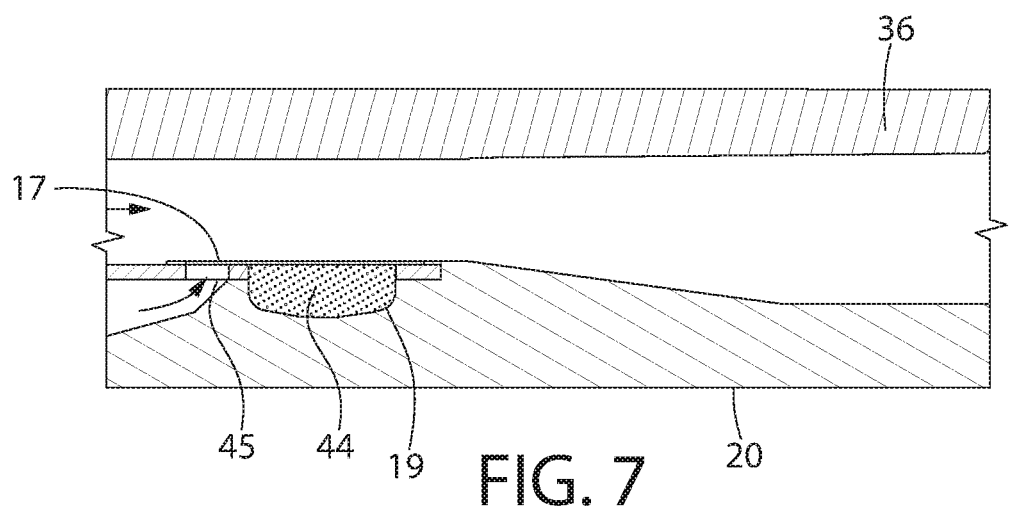
FIGS. 7-9 are sequential views of operation of lifting of a flap of the annular member and removal of powder toward a mouthpiece for inhalation by a user.
Figure 8:
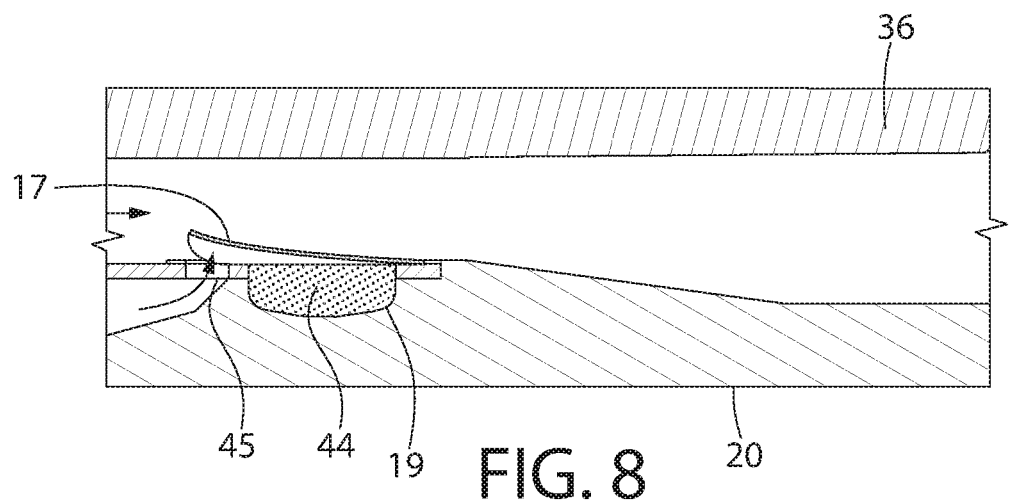
Figure 9:
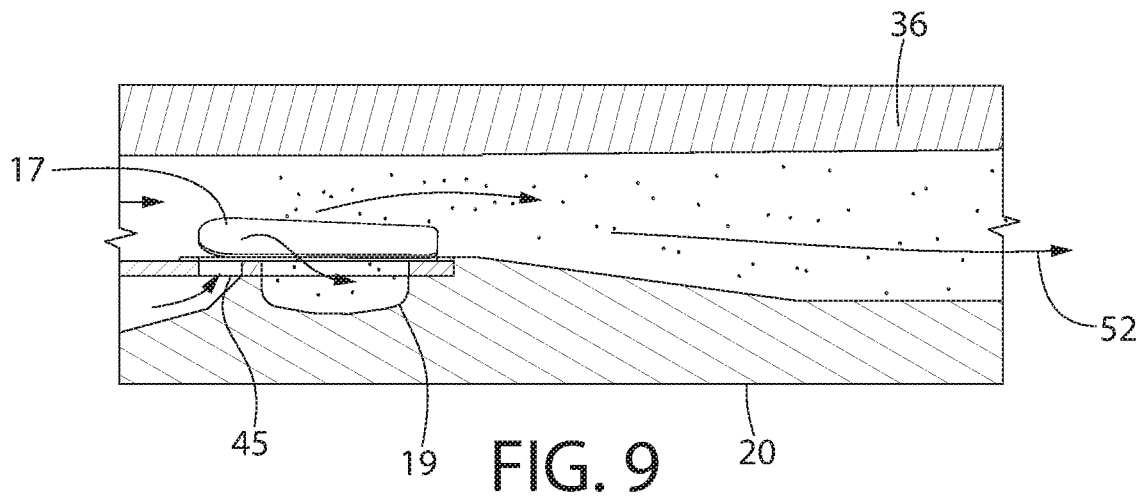

Referring now in detail to the various figures, wherein like reference numerals refer to like parts throughout, FIGS. 1-9 illustrate one embodiment of a device or inhaler, generally designated 10, for facilitating inhalation of powder, such as dry powder medicament 44 or powder with API (see FIGS. 7-9). The inhaler 10 can include a body 25 having an end cap 23 at one end thereof and a mouthpiece 26 at an opposing end thereof. End cap 23 can include or be formed of an active material 24 (e.g., desiccant), as described in detail below. The body 25 defines or surrounds an interior space, and the mouthpiece 26 can define a pathway that is fluidly connected to the interior space of the body 25. The mouthpiece 26 allows a user to draw or inhale air containing the powder.

The dry powder medicament 44 can be any of a variety of formulations or compositions. In fact, any medications, pain or fever reducers and/or anti-inflammatory drugs that are available as inhaled treatments can be used. Optionally, the dry powder medicament 44 can be useful or beneficial for individuals with asthma, chronic obstructive pulmonary disease (COPD), bronchitis, emphysema, cystic fibrosis (CF) and/or any lung deficiency, infection or symptom. In one embodiment, the dry powder medicament 44 can include one or more excipients, organic co-solvents (e.g., used to enhance the solubility of the drug substance), peptides, proteins, and/or carriers (e.g., lactose). Optionally, the medicament 44 can be in aerosol form. U.S. Pat. No. 9,585,834, which discusses various dry powder compositions, is hereby incorporated by reference in its entirety. The inhaler 10 is particularly effective in dispensing and/or allowing a user to receive selective, small doses of the dry powder medicament 44.

A cover 28 can be removably and/or pivotally attached to the body 25. In one embodiment, the cover 28 is attached via a hinge to the body 25. The cover 28 can be movable with respect to the body 25 between a closed position (see FIG. 1) and an open position. When the cover 28 is in the closed position, the mouthpiece 26 is covered and/or protected. When the cover 28 is in the open position, the mouthpiece 26 is exposed and able to be engaged or contacted by the user. The cover 28 can include a pivotable trigger 27, as described in more detail below.

Optionally, one or more of the body 25, the end cap 23 and the cover 28 can be formed of a low moisture vapor transfer (LMVT) rate plastic. The LMVT rate material reduces moisture ingress during storage and use of the device 10. When closed and/or fully attached (see FIG. 1), the combined body 25, end cap 23 and cover 28 form a tightly sealed DPI. By designing a tightly sealed DPI device and using desiccant plastic for controlling moisture within it, improved powder dispersion and reduced capillary forces can be expected as compared to the prior art.

In one embodiment, the inhaler 10 includes only nine parts, eight of which are injection molded. This design removes the need for piercing the material securing the powder prior to dispersing the powder, which is required by some prior art designs. The design of the presently disclosed technology also eliminates the risk of contaminating the drug formulation with debris from a piercing mechanism.

Figure 1:
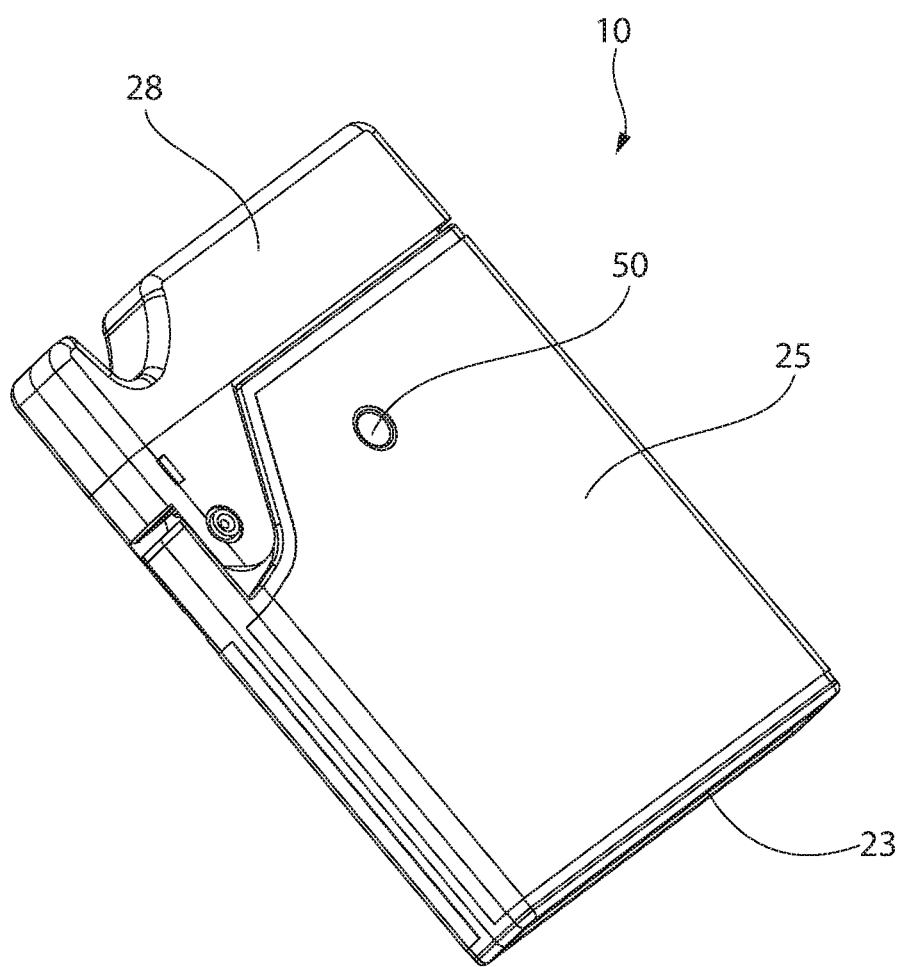
FIG. 1 is a perspective view of an inhaler according to an embodiment of the present disclosed technology, wherein the inhaler is shown from a first side.
Figure 2:
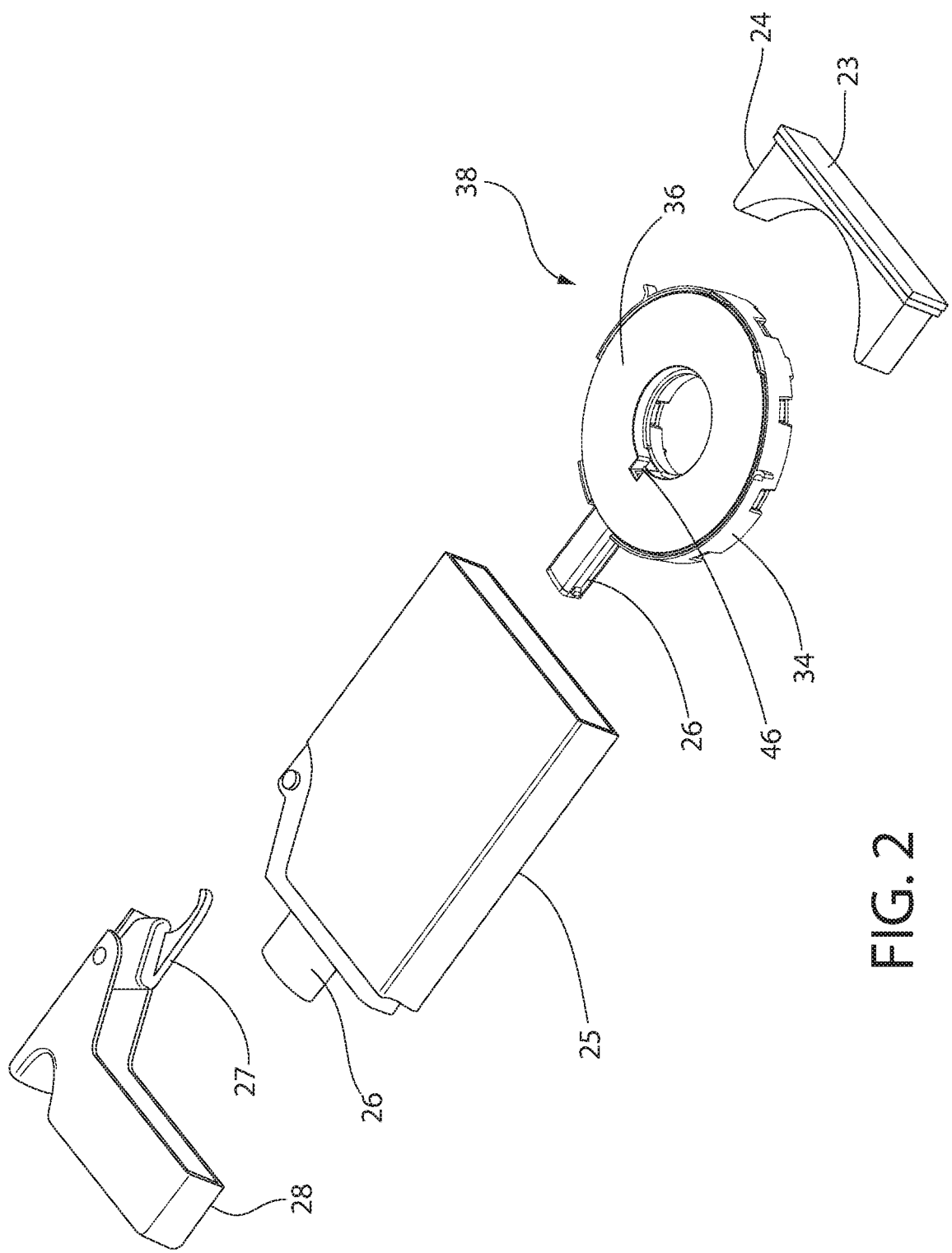
FIG. 2 is a partially exploded perspective view of the inhaler of FIG. 1, wherein the inhaler is shown from an opposite second side.
Figure 3:
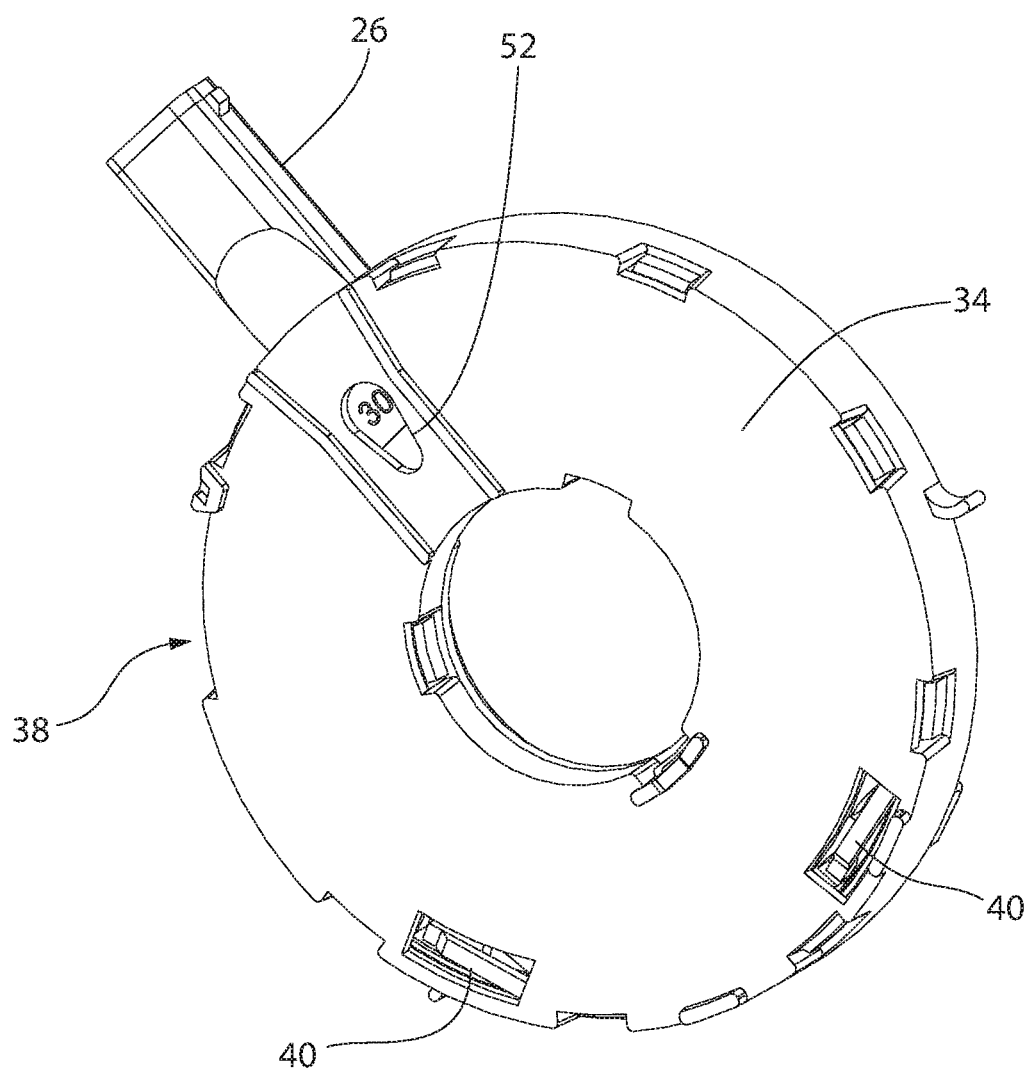
FIG. 3 is a perspective view of at least some interior components of the inhaler shown in FIG. 2, wherein the components are shown from the first side shown in FIG. 1.
Figure 4:
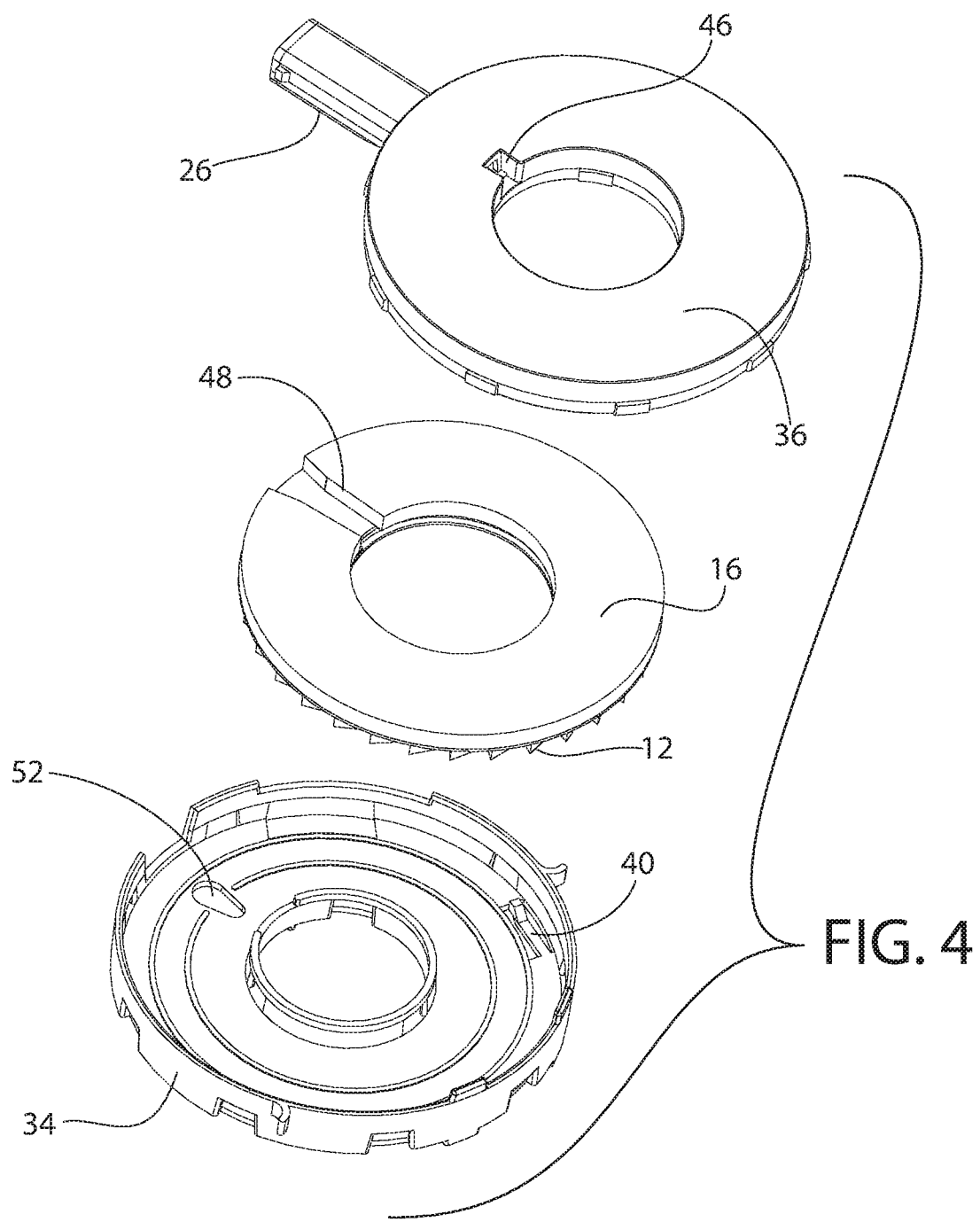
FIG. 4 is a partially exploded perspective view of the interior components shown in FIG. 2.

The inhaler 10 includes at least one member 51 positioned within the interior space of the body 25. In one embodiment, as shown in FIGS. 4-6, the at least one member 51 is an annular member or a dose ring that is rotatable with respect to the body 25. In another embodiment, the member 51 can be a linear member or a dose line. The member 51 can be configured to provide a plurality of separate doses of medicament. In yet another embodiment, the member 51 can be configured to provide only a single dose of medicament.

As shown in FIGS. 2-5, one embodiment of the annular member 51 can be supported or enclosed within the body 25 by a first tray 34 and a second tray 36. Both the first tray 34 and the second tray 36 can have a generally circular outer periphery and a generally circular inner periphery. In one embodiment, at least a portion of the second tray 36 can fit within the first tray 34. An air duct 32 (see FIG. 5) can be arranged or formed within the second tray 36 and can connect an opening 46 through a top and/or side wall of the second tray 36 to the passageway of the mouth piece 26. In one embodiment, the mouth piece 26 is an integral or unitary portion of the second tray 36.

As shown in FIG. 5, the second tray 36 can include a circular center guide 21. The annular member 51 can fit or be positioned within or between the first tray 34 and the second tray 36, and the annular member 51 can rotate with respect to both the first tray 34 and the second tray 36. More particularly, in one embodiment, the annular member 51 is placed around the center guide 21 when placed in the second tray 36. A seal or spacer 16, optionally formed of foam, can be positioned between the annular member 51 and an interior surface of the second tray 36. The spacer 16 can include an opening or cut-out 48. The spacer 16 can be arranged in the second tray 36 so that the spacer 16 is positioned on both sides of the air duct 32.

Optionally, the first tray 34 (and/or the second tray 36) can include at least one stop or spring 40 extending at least partially into an interior of the first tray 34 in a biased or relaxed state. In another embodiment, the first tray 34 can include two or more spaced-apart springs 40. Each spring 40 can inhibit rotation of the annular member 51 with respect to the first tray 34 and the second tray 36. In one embodiment, each spring 40 is a leaf spring with one end thereof integrally or unitarily formed with a base wall of the first tray 34. An interior surface of each spring 40 can include a projection or an angled surface.

Referring to FIG. 6, in one embodiment, the annular member 51 is formed of three parts or components: a first annular member 18a, a second annular member 18b, and a third annular member 20. In one embodiment, the first annular member 18a is formed of aluminum foil. Optionally, the first annular member 18a includes cuts that form a plurality of spaced-apart and generally identical hinged flaps 17. In FIG. 6, the one flap 17 identified with a reference number is shown in a partially open position, and the remaining flaps 17 are shown closed. In one embodiment, the cuts can be formed in the shape of a "C," and a hinge 47 is created by an uncut edge of each flap 17. Optionally, the first annular member 18a includes at least thirty separate flaps 17. The flaps 17 can be equidistantly spaced around the first annular member 18a, except that a blank or solid space is formed between two particular flaps 17. In one embodiment, a width of the blank space is approximately twice the width of a single flap 17.

Optionally, the first annular member 18a is bonded to an upper surface 13 (or lower surface, depending upon orientation of the device 10) of the second annular member 18b. In another embodiment, the first annular member 18a is integrally and unitarily formed with the second annular member 18b, such that the annular member 51 is only formed of two parts or components. The second annular member 18b can include a plurality of spaced-apart holes 14, each of which are aligned with one of the cuts of the first annular member 18a so as to define a passageway through the second annular member 18b when the flaps 17 are opened. The holes 14 of the second annular member 18b can be generally oval-shaped.

The third annular member 20 can include or define a plurality of spaced-apart compartments, capsules or dose pocket cavities 19. Each compartment 19 can be sized, shaped, and/or configured to hold a predetermined amount of powder, such as a daily dose of a powder medicament. Optionally, each compartment 19 can be sized to contain or hold 10-13 mg of powder 44. Each compartment 19 includes at least one opening so as to allow the powder 44 to be inserted into the compartment 19 and removed from the compartment 19 at the desired time. Each flap 17 covers the opening of the respective compartment 19, includes an extension extending beyond an outer edge of the opening when the flap 17 is in the closed position. At least a portion of an underside of the extension of each flap 17 is free or unattached to any structure.

One continuous or a plurality of spaced-apart conduits can be positioned proximate to the compartments 19, such as radially inwardly of each compartment 19. At least a portion of the underside of each flap 17 faces the associated or respective conduit(s). In one embodiment, each of the plurality of spaced-apart conduits is a hole 45 through the third annular member 20. Each hole 45 can correspond to or be positioned next to, but spaced-apart from, one of the compartments 19. In one embodiment, the opening that defines the hole 45 in the third annular member 20 is smaller than the opening of the respective compartment 19. Optionally, each hole 45 can be located next to the respective compartment 19 toward an inside edge 11 of third annular member 20. In one embodiment, each hole 45 extends through the third annular member 20, while each compartment 19 does not extend through the third annular member 20 so as to hold the medicament. In an alternative embodiment, the plurality of spaced-apart holes 45 can be replaced by a single, continuous channel or conduit that extends around and through the third annular member 20. The channel can function the same as the plurality of spaced-apart holes 45 described above.

When combined, the first, second and third annular members 18*a*, 18*b*, 20 seal the powder within the dose cavity 19 unless and until the flap 17 is opened. In one embodiment, although the cut allows each flap 17 to be opened more easily, the cut does not destroy the sealing capacity of the combined first, second and third annular members 18*a*, 18*b*, 20. In one embodiment, the first annular member 18*a* is formed of a thin layer of aluminum foil that is in-mold labeled to the second annular member 18*b* and then ultrasonically welded to the third annular member 18. Optionally, the second annular member 18*b* and the third annular member 20 can be molded plastic, such as medical-grade plastic.

In one alternative embodiment, instead of each flap 17 being associated with one of the compartments 19, as described in detail above, each flap 17 can cover and/or be associated with two or more separate and spaced-apart compartments 19. Each of these compartments 19 can contain the same type or kind of powder 44. In an alternative embodiment, at least two adjacent compartments 19 associated with one of the flaps 17 can contain different types or kinds of powder or medicament 44 that cannot or should not be mixed during storage, but can and/or should be delivered simultaneously or substantially simultaneously when inhaled by the user.

A plurality of spaced-apart ridges or teeth 12 can extend around the outer periphery of the third annular member 20. The teeth 12 can extend evenly or equidistantly spaced-apart around the entire periphery of the third annular member 20. At least a portion of the trigger 27 can contact or engage one of the teeth 12 of the annular member 51 through an opening 38 formed in a sidewall of the housing 36. The trigger 27 can be spring-loaded. Alternatively, the trigger 27 can omit the spring and simply move or rotate the annular member 51 upon opening the cover 28, such as shown in FIGS. 4A-4C of U.S. Application Publication No. 2014/0007875. Selective engagement of the trigger 27 with teeth 12 of the annular member 51 can overcome the force of each spring 40 on the annular member 51 to rotate or "advance" the annular member 51 within the combined first tray 34 and the second tray 36. Each spring 40 can provide a tactical and/or audible action in response to the trigger 27 overcoming the biasing force of each spring 40.

Referring specifically to FIGS. 1 and 3-5, the housing 25 can include a window 50 in one of the walls thereof. The first tray 34 can include an opening 52 through a base wall thereof. The opening 52 of the first tray 34 can be aligned with the window 50 when the first tray 34 is properly positioned within the housing 25. The third annular member 20 can include a plurality of spaced-apart indicia, such as chronological or consecutive numerals and/or letters (e.g., 30, 29, 28, 27, etc.). Each one of the indicia can be located proximate to one of the compartments 19, but on an opposite side from where the compartments 19 are formed.

In one embodiment, the active material 24 is a desiccant. This would be an embodiment where moisture absorption is desired. However, where moisture absorption is not desired, the active material 24 can include alternative active agents. For example, in another embodiment, the active material 24 contains a material selected from the group consisting of activated carbon, carbon black, ketcham black and diamond powder. In a further embodiment, an active agent including one or more layers of the active material 24 contains a material such as absorption microspheres, $BaTiO_3$, $SrTiO_3$, $SiO_2$, $Al_2O_3$, $ZnO$, $TiO_2$, $MnO$, $CuO$, $Sb_2O_3$, silica, calcium oxide and ion exchange resins. In yet another embodiment, an absorbing agent containing layer of the active material 24 contains two or more types of absorbing agents. The suitable absorbing agent is chosen so as to achieve absorption of the desired vapor or gas for the desired end use (e.g. absorption of moisture, oxygen, carbon dioxide, nitrogen or other undesired gases or vapors).

The active material 24 (whether desiccant, oxygen scavenger, a releasing material or agent, etc., or combination thereof) is capable of acting on, interacting or reacting with a selected material (e.g., moisture or oxygen). Examples of such actions or interactions may include absorption, adsorption (sorption, generally) or release of the selected material.

The active material 24 can include an "active agent" in a base material. The active agent (i) can be immiscible with the base material (e.g., polymer) and when mixed and heated with the base polymer and a channeling agent, will not melt, i.e., has a melting point that is higher than the melting point for either the base polymer or the channeling agent, and/or (ii) acts on, interacts or reacts with a selected material. The term "active agent" may include but is not limited to materials that absorb, adsorb or release the selected material(s). Active agents according to the presently disclosed technology may be in the form of particles such as minerals (e.g., molecular sieve or silica gel, in the case of desiccants), but the presently disclosed technology should not be viewed as limited only to particulate active agents. For example, in some embodiments, an oxygen scavenging formulation may be made from a resin which acts as, or as a component of, the active agent.

As used herein, the term "base material" is a component (preferably a polymer) of an entrained active material, other than the active agent, that provides structure for the entrained material.

As used herein, the term "base polymer" is a polymer optionally having a gas transmission rate of a selected material that is substantially lower than, lower than or substantially equivalent to, that of the channeling agent. By way of example, such a transmission rate would be a water vapor transmission rate in embodiments where the selected material is moisture and the active agent is a water absorbing desiccant. The primary function of the base polymer is to provide structure for the entrained polymer. Suitable base polymers may include thermoplastic polymers, e.g., polyolefins such as polypropylene and polyethylene, polyisoprene, polybutadiene, polybutene, polysiloxane, polycarbonates, polyamides, ethylene-vinyl acetate copolymers, ethylene-methacrylate copolymer, poly(vinyl chloride), polystyrene, polyesters, polyanhydrides, polyacrylianitrile, polysulfones, polyacrylic ester, acrylic, polyurethane and polyacetal, or copolymers or mixtures thereof.

Referring to such a comparison of the base polymer and channeling agent water vapor transmission rate, in one embodiment, the channeling agent has a water vapor transmission rate of at least two times that of the base polymer. In another embodiment, the channeling agent has a water vapor transmission rate of at least five times that of the base polymer. In another embodiment, the channeling agent has a water vapor transmission rate of at least ten times that of the base polymer. In still another embodiment, the channeling agent has a water vapor transmission rate of at least twenty times that of the base polymer. In still another embodiment, the channeling agent has a water vapor transmission rate of at least fifty times that of the base polymer. In still another embodiment, the channeling agent has a water vapor transmission rate of at least one hundred times that of the base polymer.

As used herein, the term "channeling agent" or "channeling agents" is defined as a material that is immiscible with the base polymer and has an affinity to transport a gas phase substance at a faster rate than the base polymer. Optionally, a channeling agent is capable of forming channels through the entrained polymer when formed by mixing the channeling agent with the base polymer. Optionally, such channels are capable of transmitting a selected material through the entrained polymer at a faster rate than in solely the base polymer.

As used herein, the term "channels" or "interconnecting channels" is defined as passages formed of the channeling agent that penetrate through the base polymer and may be interconnected with each other.

As used herein, the term "entrained polymer" is defined as a monolithic material formed of at least a base polymer with an active agent and optionally also a channeling agent entrained or distributed throughout. An entrained polymer thus includes two-phase polymers and three-phase polymers. A "mineral loaded polymer" is a type of entrained polymer, wherein the active agent is in the form of minerals, e.g., mineral particles such as molecular sieve or silica gel. The term "entrained material" is used herein to connote a monolithic material comprising an active agent entrained in a base material wherein the base material may or may not be polymeric.

As used herein, the term "monolithic," "monolithic structure" or "monolithic composition" is defined as a composition or material that does not consist of two or more discrete macroscopic layers or portions. Accordingly, a "monolithic composition" does not include a multi-layer composite.

As used herein, the term "phase" is defined as a portion or component of a monolithic structure or composition that is uniformly distributed throughout, to give the structure or composition it's monolithic characteristics.

As used herein, the term "selected material" is defined as a material that is acted upon, by, or interacts or reacts with an active agent and is capable of being transmitted through the channels of an entrained polymer. For example, in embodiments in which a desiccant is used as an active agent, the selected material may be moisture or a gas that can be absorbed by the desiccant. In embodiments in which a releasing material is used as an active agent, the selected material may be an agent released by the releasing material, such as moisture, fragrance, or an antimicrobial agent (e.g., chlorine dioxide). In embodiments in which an adsorbing material is used as an active agent, the selected material may be certain volatile organic compounds and the adsorbing material may be activated carbon.

As used herein, the term "three phase" is defined as a monolithic composition or structure comprising three or more phases. An example of a three phase composition according to the presently disclosed technology would be an entrained polymer formed of a base polymer, active agent, and channeling agent. Optionally, a three phase composition or structure may include an additional phase, e.g., a colorant.

Entrained polymers may be two phase formulations (i.e., comprising a base polymer and active agent, without a channeling agent) or three phase formulations (i.e., comprising a base polymer, active agent and channeling agent). Entrained polymers are described, for example, in U.S. Pat. Nos. 5,911,937, 6,080,350, 6,124,006, 6,130,263, 6,194,079, 6,214,255, 6,486,231, 7,005,459, and U.S. Pat. Pub. No. 2016/0039955, each of which is incorporated herein by reference in its entirety.

An entrained material or polymer includes a base material (e.g., polymer) for providing structure, optionally a channeling agent and an active agent. The channeling agent forms microscopic interconnecting channels through the entrained polymer. At least some of the active agent is contained within these channels, such that the channels communicate between the active agent and the exterior of the entrained polymer via microscopic channel openings formed at outer surfaces of the entrained polymer. The active agent can be, for example, any one of a variety of absorbing, adsorbing or releasing materials, as described in further detail below. While a channeling agent is preferred, the invention broadly includes entrained materials that optionally do not include channeling agents, e.g., two phase polymers.

In any embodiment, suitable channeling agents may include a polyglycol such as polyethylene glycol (PEG), ethylene-vinyl alcohol (EVOH), polyvinyl alcohol (PVOH), glycerin polyamine, polyurethane and polycarboxylic acid including polyacrylic acid or polymethacrylic acid. Alternatively, the channeling agent can be, for example, a water insoluble polymer, such as a propylene oxide polymerisate-monobutyl ether, such as Polyglykol B01/240, produced by CLARIANT. In other embodiments, the channeling agent could be a propylene oxide polymerisate monobutyl ether, such as Polyglykol B01/20, produced by CLARIANT, propylene oxide polymerisate, such as Polyglykol D01/240, produced by CLARIANT, ethylene vinyl acetate, nylon 6, nylon 66, or any combination of the foregoing.

Suitable active agents according to the presently disclosed technology include absorbing materials, such as desiccating compounds. If the active agent is a desiccant, any suitable desiccant for a given application may be used. Typically, physical absorption desiccants are preferred for many applications. These may include molecular sieves, silica gels, clays and starches. Alternatively, the desiccant may be a chemical compound that forms crystals containing water or compounds which react with water to form new compounds.

Optionally, in any embodiment, the active agent may be an oxygen scavenger, e.g., an oxygen scavenging resin formulation.

Table 1 below shows the characterization of the designed desiccant moisture adsorption capacity and the consumption of the capacity due to moisture ingress into the device following exposure to calculated moisture amounts at various stages of manufacturing, storage, and use of the DPI device of one embodiment of the presently disclosed technology.

TABLE 1

Moisture ingress and consumption of desiccant moisture adsorption capacity

| | Stage Desiccant Plastic Part/DPI Device | | | | | | | |
|---|---|---|---|---|---|---|---|---|
| | Design | Molding | Storage | Assembly | Shelf-Life | Use-Life | 30 Uses | Remaining |
| Moisture Ingress, mg | N/A | 6 | 160 | 8 | 130 | 306 | 10 | N/A |
| Desiccant Moisture Adsorption Capacity, mg | 750 | 744 | 584 | 576 | 446 | 140 | 130 | 130 |

The following are assumptions used for calculating the moisture ingress during the various stages of manufacturing the device described in Table 1 above:

Adsorption:

3,000 μg of water vapor is adsorbed in the molded desiccant part in 1 hour. In addition, 0.3 mg of latent moisture in molded plastic parts and PE Seal need to be adsorbed following device assembly.

Molding:

molded desiccant plastic parts are exposed for at least 1 or 2 hours during molding before being placed in a foil bag that is sealed. (25° C./60% Relative Humidity (RH) Conditions).

Storage at Molding Facility:

molded desiccant plastic parts are stored in sealed foil bags within a poly bag in shipping cartons. (25° C./60% RH Conditions).

Storage at Assembly Site:

molded desiccant plastic parts are stored at Assembly Site for 1 year before parts are used for manufacturing devices. (25° C./60% RH Conditions)

Assembly:

molded desiccant plastic parts are exposed for 2 hours during manufacturing as completed devices at Assembly Site and placed individually into a foil pouch that is sealed. Note: latent moisture in molded plastic parts and PE Seal are adsorbed following device assembly. (25° C./60% RH Conditions).

Shelf-Life:

manufactured device is stored in a sealed foil pouch for 1 year before being opened for use. (30° C./75% RH Conditions).

Use-Life:

device is stored closed during 60 days and available for use. (30° C./75% RH Conditions).

30 Uses:

device is opened and re-closed 30 times over the 60 days of Use-Life. (30° C./75% RH Conditions).

FIGS. 7-9 show operation of one embodiment of the device 10. For example, once the user engages the trigger 27 to rotate the annular member 51 to the desired position (e.g., when the correct day or dosage period is visible through the opening 52 of the first tray 34 and the window 50 of the housing 25, the user can inhale through the mouth piece 26. In one embodiment, this causes air to travel simultaneously through two separate paths, namely (i) from beneath and through the hole 45 that is positioned within the air duct 32 of the first tray 34 and (ii) through the opening 46 (see FIGS. 2, 4 and 5) of the second tray 36 and then above the hole 45 and the compartment 19 within the air duct 32 of the first tray 34. In contrast to prior art designs, air flow in one embodiment of the presently disclosed technology is directed through one of the holes 45, which exerts pressure on a bottom surface of one of the flaps 17 to cause it to open. The size, shape and/or configuration of the air duct 32 can be modified or adjusted for different pathologies or different parts of the population (e.g., children or elderly).

The combination of air flow described above reliably and effectively moves the flap 17 aligned with or within the air duct 32 of the third tray 34 from the closed position to the opened position, thereby allowing the powder in the compartment 19 to be released or withdrawn by the Venturi effect and travel to the user's mouth through the mouth piece 36. The spacer 16 is configured to maintain all of the flaps 17 not aligned with or within the air duct 32 of the third tray 34 in a closed position. Thus, the spacer 16 can maintain each the flaps 17 in a closed configuration, except where the opening 48 is aligned with the air duct 32. Any flap 17 positioned directly beneath or above the opening 48 can be opened upon a force exerted by the user. In certain embodiments, the spacer 16 can have a thickness of approximately 0.062 inches, 0.093 inches, or 0.125 inches, depending upon the force required to open the flaps 17 and/or the medicament used.

Figure 10:
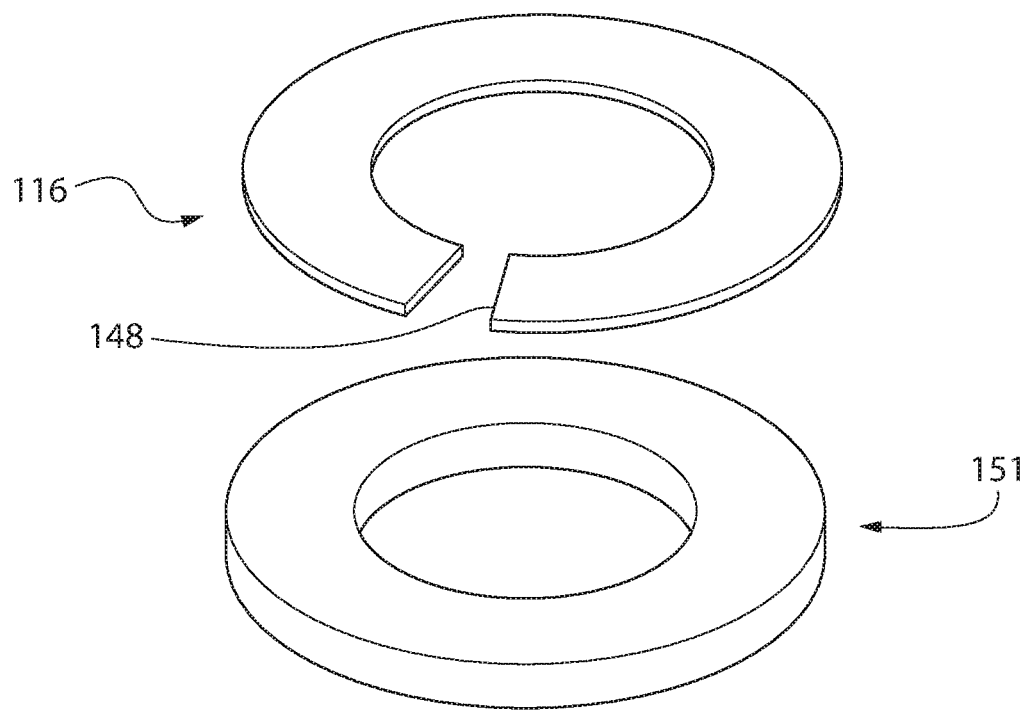
FIG. 10 is an exploded perspective schematic view of two components of an inhaler according to an embodiment of the presently disclosed technology.
Figure 11:
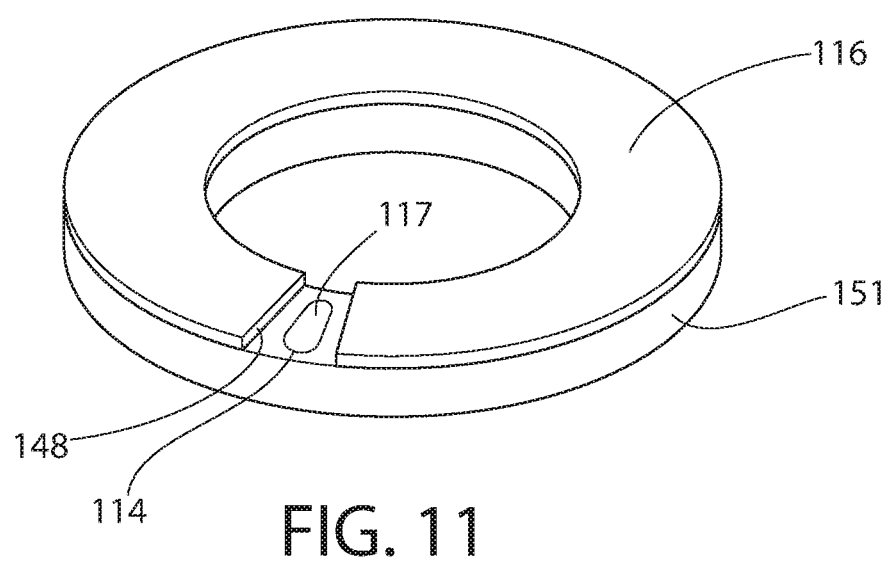
FIG. 11 is a perspective schematic view of the components shown in FIG. 10, wherein the components are shown in a use position.

FIGS. 10 and 11 show another embodiment of the presently disclosed technology. Similar or identical structure between the embodiments of FIGS. 1-9 and FIGS. 10-11 is distinguished in FIGS. 10-11 by a reference number with a magnitude one hundred (100) greater than that of FIGS. 1-9. Description of certain similarities between the embodiments may be omitted herein for convenience and brevity only.

In operation, the seal or spacer 116 is in contact with the annular member 151 to ensure that medicament stays in each compartment that is enclosed by the spacer 116. Because of the cut-out 148, only one of the chambers is exposed, such that the flap 117 can expose the opening 114 when a sufficient flow of air is supplied.

Figure 12:
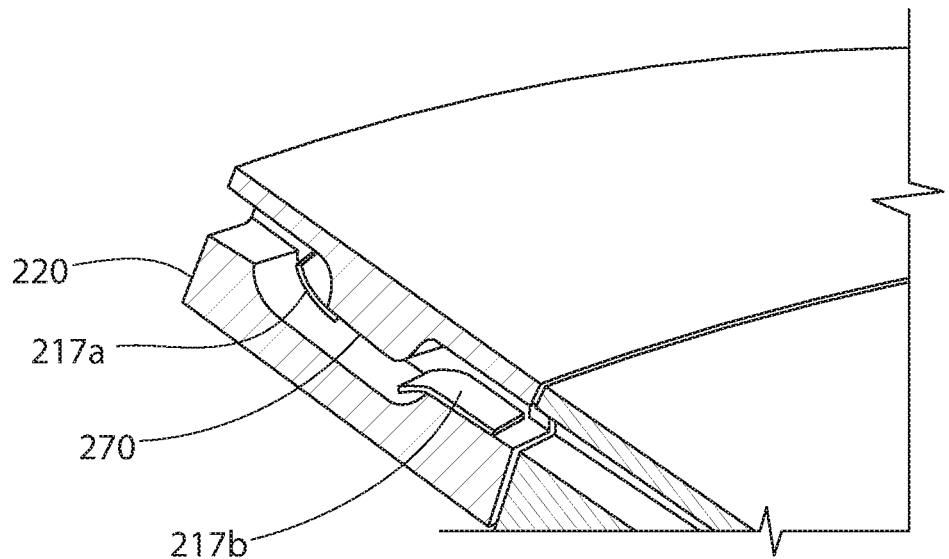
FIG. 12 is a cross-sectional perspective view of a portion of an inhaler according to an embodiment of the presently disclosed technology, wherein two flaps are shown in an open position or configuration.
Figure 13:
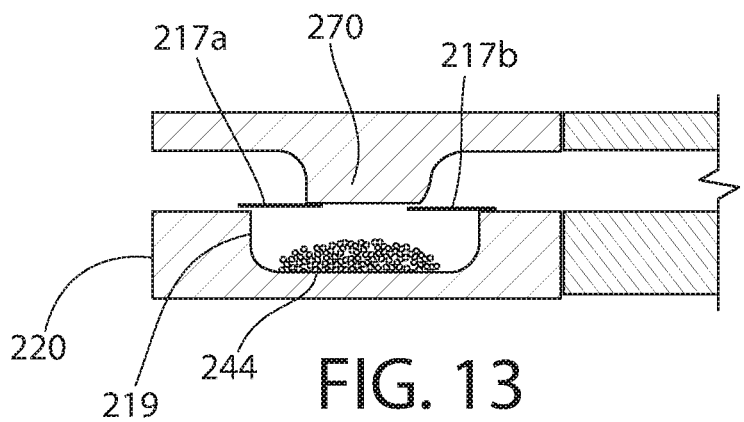
FIG. 13 is a cross-sectional side elevation view of the inhaler shown in FIG. 12, wherein the flaps are shown in a closed position.
Figure 14:
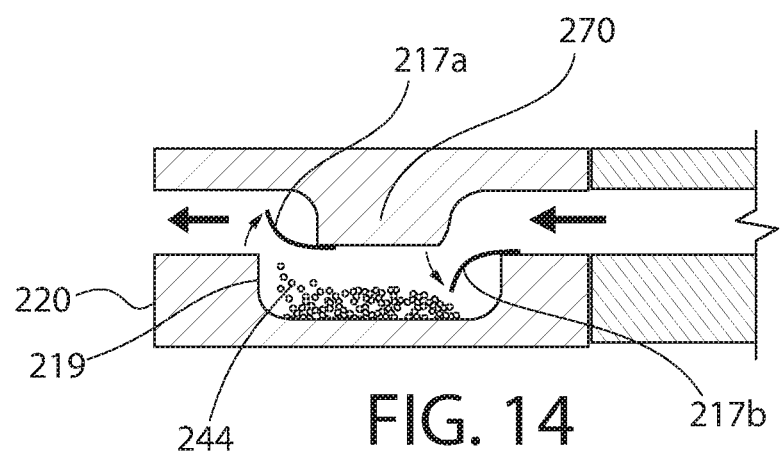
FIG. 14 is another cross-sectional side elevation view of the inhaler shown in FIG. 12, wherein the flaps are shown in the open position.

FIGS. 12-14 show another embodiment of the presently disclosed technology. Similar or identical structure as between the embodiments of FIGS. 1-9 and FIGS. 12-14 is distinguished in FIGS. 12-14 by a reference number with a magnitude two hundred (200) greater than that of FIGS. 1-9. Description of certain similarities between the earlier embodiments and the embodiment of FIGS. 12-14 may be omitted herein for convenience and brevity only.

The annular member 220 of the present embodiment may include only a single component, as compared to the first, second and third annular members 18a, 18b, 20 of the first embodiment described above. In the present embodiment, each compartment 219 can include two spaced-apart flaps 217a, 217b. Each flap 217a, 217b can be positioned proximate to a top of the respective compartment 219. Optionally, one of the flaps 217a is closer to the mouthpiece or outer periphery of the inhaler and the other flap 217b is closer to a geometric center of the inhaler.

In one embodiment, each flap 217a, 217b is formed of a flexible or resilient material, such as foil or aluminum foil. Optionally, the foil can have a thickness of approximately 20-25 microns. Each flap 217a, 217b is movable or reconfigurable between an open configuration (see FIGS. 12 and 14) and a closed configuration (see FIG. 13). Optionally, each flap 217a, 217b is biased to the closed position. In the closed position, in one embodiment, each flap 217a, 217b is linear or extends in a single plane (see FIG. 13). In the open position, in one embodiment, each flap 217a, 217b is arcuate or curved (see FIG. 14). Each flap 217a, 217b can be moved from the closed position to the open position by a user inhaling through the mouthpiece, for example.

At least one projection 270 can extend downwardly from an interior of the device (e.g., from the spacer or body). Each flap 217a, 217b can extend from an edge of the respective compartment 219 to the projection 270. Optionally, a first or lower side of each flap 217a, 217b contacts the edge of the respective compartment 219 and an opposing second or upper side of each flap 217a, 217b contacts the projection 270. When a sufficient amount of air flow is caused to travel through the inhaler (e.g., by a user inhaling at the mouthpiece), the inner flap 217b is pushed downwardly into the compartment 219 and the outer flap 217a is pushed upwardly out of the compartment 219, thereby causing the medicament 244 to be picked-up by the air flow in the direction of the mouthpiece. In addition to combining with the flaps 217a, 217b to close the compartment 219 when the flaps 217a, 217b are in the closed position, the projection 270 can serve to guide or direct the air stream down into the compartment 219.

Figure 15:
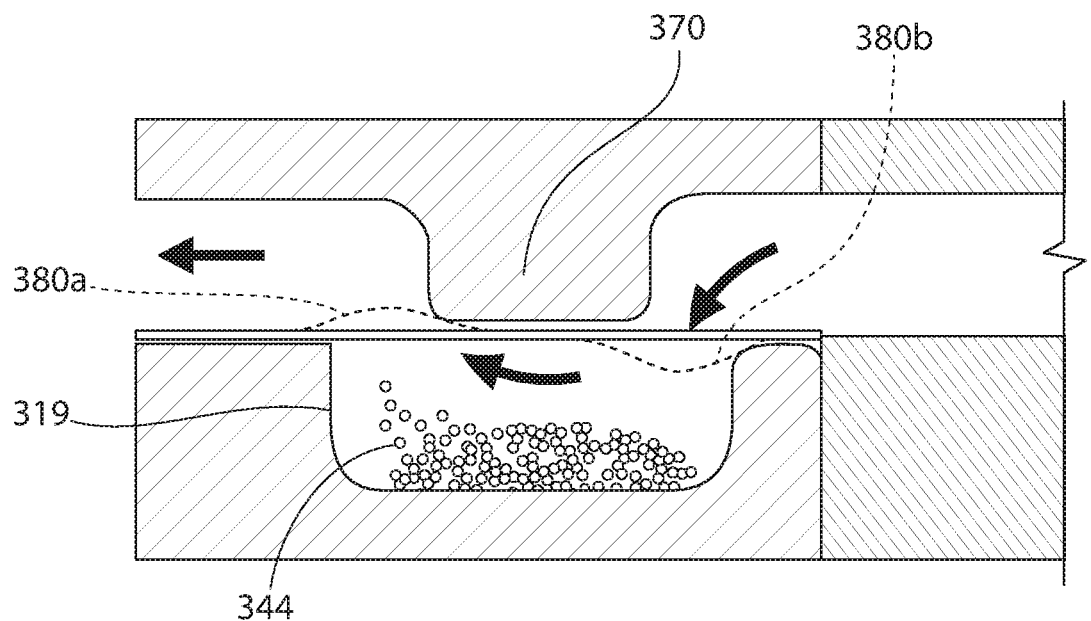
FIG. 15 is a cross-sectional side elevation view of a portion of an inhaler according to an embodiment of the presently disclosed technology.
Figure 16A:
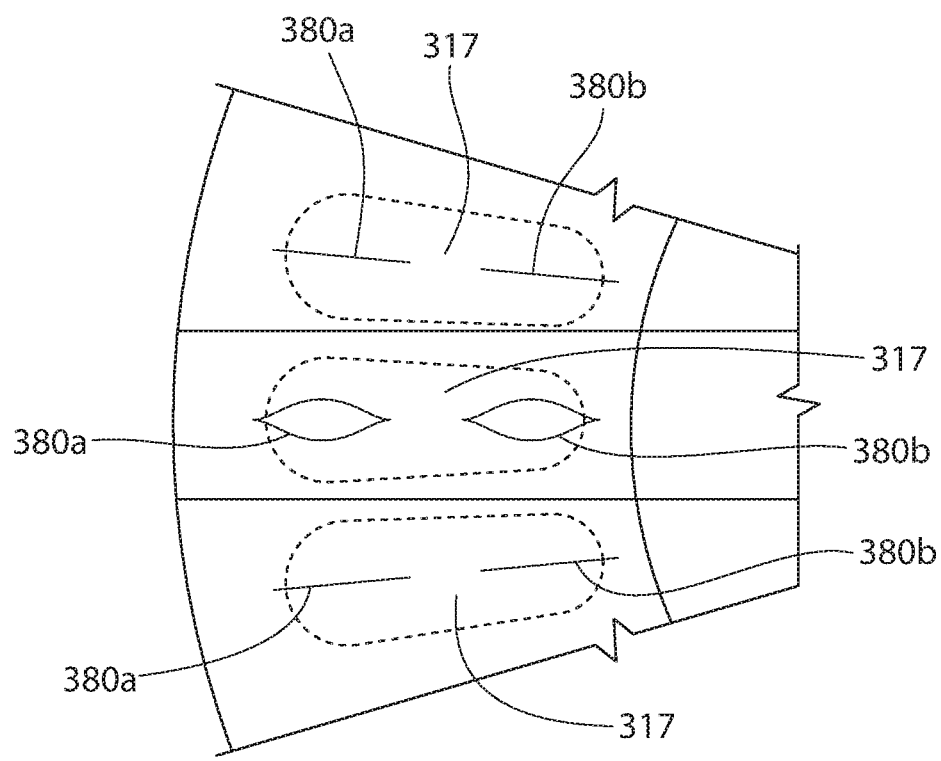
FIG. 16A is a top plan view of a plurality of the flaps shown in FIG. 15, wherein the upper and lower-most flaps shown in FIG. 16 are in a closed position and the middle flaps are shown in an open position.
Figure 16B:
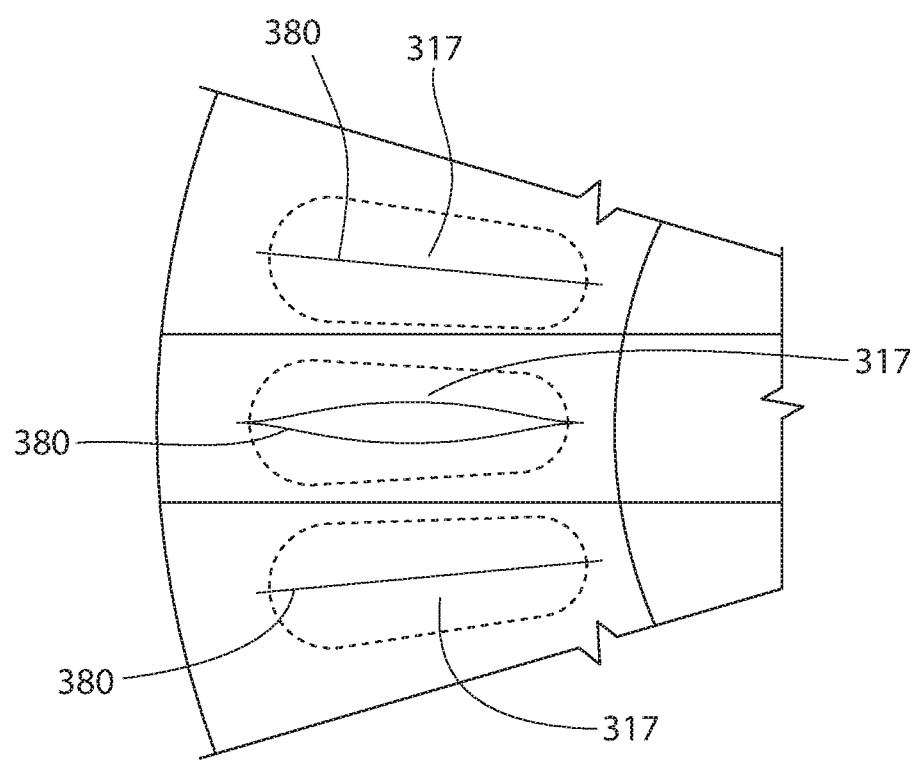
FIG. 16B is a top plan view of an alternative embodiment of the plurality of the flaps shown in FIG. 16A.

FIGS. 15-16B show other embodiments of the presently disclosed technology. Similar or identical structure as between the embodiments of FIGS. 1-9 and FIGS. 15-16B is distinguished in FIGS. 15-16B by a reference number with a magnitude three hundred (300) greater than that of FIGS. 1-9. Description of certain similarities between the earlier embodiments and the embodiment of FIGS. 15-16B may be omitted herein for convenience and brevity only.

In one aspect, as shown in FIGS. 15 and 16A, each flap 317 of the present embodiment can include two spaced-apart slots 380a, 380b. Optionally, one of the slots 380a is closer to the mouthpiece or outer periphery of the inhaler and the other slot 380b is closer to a geometric center of the inhaler. In one embodiment, each slot 380a, 380b is an incision in the respective flap 317 and extends parallel to the air flow when the respective flap 317 is positioned within the cut-out of the spacer (not shown).

Each slot 380a, 380b can be movable between a closed position and an open position. In the closed position, opposing edges of each slot 380a, 380b are in contact so as to prevent or inhibit the powder or medicament 344 from passing therethrough. In the open position, each slot 380a, 380b is at least slightly widened so that opposing edges are not in contact so as to permit the powder or medicament 344 to pass therethrough.

Optionally, at least one projection 370 can extend downwardly from an interior of the device. Each pair or set of slots 380a, 380b can be position on opposing sides of the projection 370. The projection 370 can serve to guide or direct the air stream down to the first slot 380b and/or into the compartment 319.

In operation, when any pair of slots 380a, 380b is positioned within the air stream or the cut-out of the spacer (not shown), one of the slots 380b can open downwardly into the compartment 319 when a sufficient flow of air is supplied through the inhaler (e.g., by a user inhaling from the mouthpiece), and the other one of the slots 380a can open upwardly away from the compartment 319.

In another aspect, as shown in FIG. 16B, each flap 317 of the present embodiment can include one or at least one slot 380. Optionally, the slot 380 can extend across the entire compartment 319, for example parallel to a length of the compartment 319. Optionally, this aspect can include (or omit) the projection discussed above and shown in FIG. 15.

Figure 17:
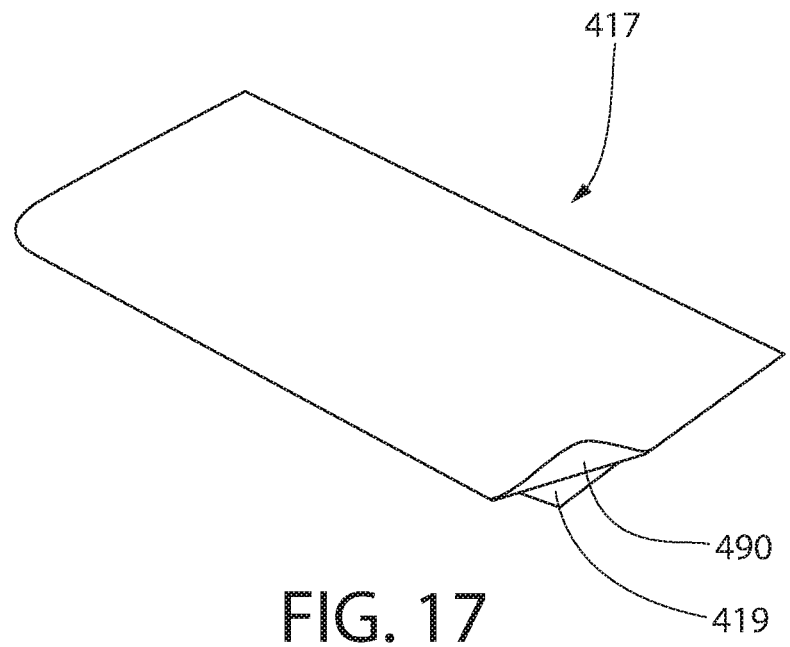
FIG. 17 is a perspective view of a portion of flap of an inhaler according to an embodiment of the presently disclosed technology, wherein the flap includes an edge biased in an upward position.
Figure 18:
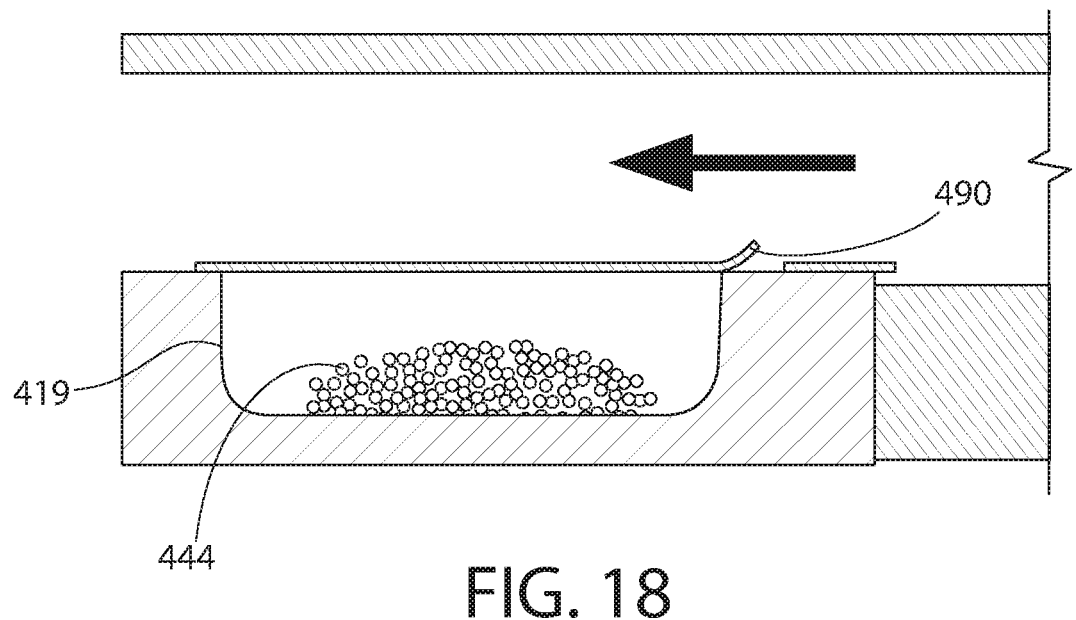
FIG. 18 is a perspective view of the flap and part of the associated inhaler shown in FIG. 17, wherein the flap is shown in a closed position.

FIGS. 17-18 show another embodiment of the presently disclosed technology. Similar or identical structure as between the embodiments of FIGS. 1-9 and FIGS. 17-18 is distinguished in FIGS. 17-18 by a reference number with a magnitude four hundred (400) greater than that of FIGS. 1-9. Description of certain similarities between the earlier embodiments and the embodiment of FIGS. 17-18 may be omitted herein for convenience and brevity only.

Each flap 417 of the present embodiment can extend in a first plane and can include at least one portion or corner 490 that extends upwardly or is biased in an upward direction. The corner 490 can be designed to catch or receive at least a portion of the air flow traveling across the top of the flap 417, which, in turn, can cause the flap 417 to more easily and/or quickly move from a closed position (see FIGS. 17 and 18) to an open position (in which the compartment 419 is exposed) to allow the medicament 444 to be consumed by the user. Optionally, each flap 417 can have a rectangular shape when viewed from above. In addition, in one embodiment, in a closed position, at least an outer periphery of the bottom surface of each flap 417 contacts an entire outer edge of the respective compartment.

Optionally, each flap 417 (or a portion thereof) can be formed of a material having a predetermined elastic modulus. In one embodiment, each flap 417 is formed of foil or aluminum foil. Optionally, the foil used to form each flap 417 can have an elastic modulus of approximately 69 gigapascals (GPa). Such a design allows each flap 417 to retain the position shown in FIGS. 17 and 18 unless a sufficient amount of force is supplied to the corner 490 or an air flow of a sufficient speed travels across the flap 417. Optionally, at least a portion of the corner 490 or the entire corner 490 is formed of a different material than a remainder of the flap 417.

FIGS. 19A-C show another embodiment of the presently disclosed technology. Similar or identical structure as between the embodiments of FIGS. 1-9 and FIGS. 19A-C is distinguished in FIGS. 19A-C by a reference number with a magnitude five hundred (500) greater than that of FIGS. 1-9. Description of certain similarities between the earlier embodiments and the embodiment of FIGS. 19A-C may be omitted herein for convenience and brevity only.

A distinguishing feature of the present embodiment is that an entire lateral or leading side or edge 596 of each flap 517 can extend or protrude upwardly from the annular member 520 or a portion of the foil that surrounds each compartment 519. Optionally, as shown in FIG. 19C, a height h by which the edge 596 can extend above the surrounding surface is 0.2-0.3 mm. As shown in FIG. 19A, in one embodiment, each flap 517 moves from the closed position to the open position in a direction perpendicular to a direction in which the air flow moves. Optionally, as each flap 517 moves from the closed position to the open position, a radius of curvature of a top surface of the flap 517 decreases. In contrast to at least some of the other embodiments above, in the present embodiment only one lateral or following side or edge of each flap 517 has no perforations and/or is not detached from a remainder of the layer or foil that forms the flap 517.

While the presently disclosed technology has been described in detail and with reference to specific examples thereof, it will be apparent to one skilled in the art that various changes, omissions and modifications can be made therein without departing from the spirit and scope thereof. It is understood, therefore, that the presently disclosed technology is not limited to the particular embodiments disclosed, but it is intended to cover modifications within the spirit and scope of the present presently disclosed technology as defined by the appended claims.

What is claimed is:

1. An inhaler for facilitating inhalation of dry powder, the inhaler comprising:
    a body defining an interior space and including a mouth piece, at least one projection extending downwardly from an interior of the body, an entirety of the at least one projection being fixed with respect to the body; and
    at least one member within the interior space of the body, the at least one member including at least one compartment defining a cavity configured to hold dry powder, the at least one compartment including two flaps and an opening configured to release the dry powder when each of the two flaps is reconfigured from a closed position to an open position, the two flaps and the at least one projection combining to cover the opening and inhibit the dry powder from being released from the cavity when both of the two flaps are in the closed position.

2. The inhaler of claim 1, wherein the at least one member is at least one annular member that is rotatable with respect to the mouthpiece.

3. The inhaler of claim 1, wherein one of the two flaps opens into the cavity and the other of the two flaps opens out from the cavity.

4. The inhaler of claim 1, wherein each of the two flaps contacts an outer edge of the compartment and the at least one projection of the inhaler.

5. The inhaler of claim 1, wherein the body contains desiccant.

6. The inhaler of claim 1, wherein an outer periphery of the at least one member includes teeth.

7. The inhaler of claim 6, wherein the body further includes a trigger that extends into the interior space of the body, and wherein at least a distal end of the trigger contacts one of the teeth of the at least one annular member.

8. An inhaler for facilitating inhalation of dry powder, the inhaler comprising:
    a body defining an interior space and including a mouth piece; and
    at least one member within the interior space of the body, the at least one member including at least one compartment defining a cavity configured to hold dry powder, the at least one compartment including at least one flap and an opening configured to release the dry powder when at least one slot of the at least one flap are is reconfigured from a closed position to an open position, the at least one slot being an incision in the at least one flap and is in the open position when opposing edges thereof are at least slightly widened so as not to be in contact, the at least one flap covering the opening and inhibiting the dry powder from being released from the cavity when the at least one slot of the at least one flap is in the closed position.

9. The inhaler of claim 8, wherein the at least one slot includes two spaced-apart slots, and wherein one of the two slots is closer to an outer periphery of the inhaler and the other one of the two slots is closer to a center of the inhaler.

10. The inhaler of claim 9, wherein the slots are located on opposing sides of the projection of the inhaler.

11. The inhaler of claim 9, wherein the two slots include a first slot and a second slot, wherein the first slot opens into the cavity and the second slot opens out from the cavity.

12. An inhaler for facilitating inhalation of dry powder, the inhaler comprising:
    a body defining an interior space and including a mouth piece; and
    at least one member within the interior space of the body, the at least one member including at least one compartment defining a cavity configured to hold dry powder, the at least one compartment including at least one flap and an opening configured to release the dry powder when the at least one flap is reconfigured from a closed position to an open position, the at least one flap covering the opening and inhibiting the dry powder from being released from the cavity in the closed position, the at least one flap extending in a first plane, corner or an entire lateral edge of the at least one flap extending upwardly away from the plane and the cavity when the at least one flap is in the closed position, the corner or the entire lateral edge being configured to catch or receive at least a portion of air flow traveling across the top of the at least one flap to facilitate opening of the at least one flap from the closed position to the open position.

13. The inhaler of claim 12, wherein a bottom surface of at east a portion of the at least one flap contacts an outer edge of the compartment.

14. A method of effectively administering one or more small doses of a medicament for the treatment of one of asthma, chronic obstructive pulmonary disease (COPD), bronchitis, emphysema and cystic fibrosis (CF), the medicament being contained in an inhaler, the inhaler including a body defining an interior space and including a mouth piece, at least one projection extending downwardly from an interior of the body, an entirety of the at least one projection being fixed with respect to the body, at least one member within the interior space of the body, the at least one member including at least one compartment defining a cavity configured to hold dry powder, the at least one compartment including two flaps and an opening configured to release the dry powder when each of the two flaps is reconfigured from a closed position to an open position, the two flaps and the at least one projection combining to cover the opening and inhibiting the dry powder from being released from the cavity when both of the two flaps are in the closed position, the method comprising:
    inhaling or evacuating air from within the interior space of the body of the inhaler through the mouth piece of the inhaler, thereby causing air to reconfigure each of the two flaps within the body of the inhaler from the dosed position to the open position and force at least some of the medicament out of the cavity beneath the two flaps and through the mouth piece.

* * * * *